United States Patent
Yanagawa et al.

(10) Patent No.: US 9,573,864 B2
(45) Date of Patent: Feb. 21, 2017

(54) METHOD OF PRODUCING MONOCYCLIC AROMATIC HYDROCARBONS

(75) Inventors: Shinichiro Yanagawa, Tokyo (JP); Masahide Kobayashi, Tokyo (JP); Yasuyuki Iwasa, Tokyo (JP); Ryoji Ida, Tokyo (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 456 days.

(21) Appl. No.: 14/006,986

(22) PCT Filed: Mar. 23, 2012

(86) PCT No.: PCT/JP2012/057501
§ 371 (c)(1),
(2), (4) Date: Sep. 24, 2013

(87) PCT Pub. No.: WO2012/133180
PCT Pub. Date: Oct. 4, 2012

(65) Prior Publication Data
US 2014/0024871 A1    Jan. 23, 2014

(30) Foreign Application Priority Data
Mar. 25, 2011   (JP) .................................. 2011-067877

(51) Int. Cl.
| | |
|---|---|
| *C07C 4/06* | (2006.01) |
| *C10G 45/60* | (2006.01) |
| *C10G 11/18* | (2006.01) |
| *C10G 45/70* | (2006.01) |
| *C10G 47/00* | (2006.01) |
| *C10G 47/20* | (2006.01) |

(52) U.S. Cl.
CPC ................ *C07C 4/06* (2013.01); *C10G 11/18* (2013.01); *C10G 45/60* (2013.01); *C10G 45/70* (2013.01); *C10G 47/00* (2013.01); *C10G 47/20* (2013.01); *C10G 2300/1044* (2013.01); *C10G 2300/1048* (2013.01); *C10G 2300/1051* (2013.01); *C10G 2300/1055* (2013.01); *C10G 2300/1096* (2013.01); *C10G 2300/301* (2013.01); *C10G 2300/4025* (2013.01); *C10G 2400/30* (2013.01)

(58) Field of Classification Search
CPC ......... C10G 45/60; C10G 45/70; C10G 11/18; C10G 47/00; C10G 47/20; C07C 4/06
See application file for complete search history.

(56) References Cited

U.S. PATENT DOCUMENTS

| | | | | |
|---|---|---|---|---|
| 3,491,019 | A | * | 1/1970 | Hilfman ................. C10G 45/50 208/143 |
| 3,755,141 | A | | 8/1973 | Youngblood et al. |
| 4,585,545 | A | | 4/1986 | Yancey, Jr. et al. |
| 5,582,711 | A | | 12/1996 | Ellis et al. |
| 2009/0314683 | A1 | * | 12/2009 | Matsushita ............. B01J 29/48 208/111.3 |

FOREIGN PATENT DOCUMENTS

| | | |
|---|---|---|
| EP | 0038140 A1 | 10/1981 |
| EP | 0212788 A1 | 3/1987 |
| EP | 2617697 A1 | 7/2013 |
| GB | 1287722 A | 9/1972 |
| JP | S56-157488 A | 12/1981 |
| JP | S61-148295 A | 7/1986 |
| JP | S61-283687 A | 12/1986 |
| JP | H03-002128 A | 1/1991 |
| JP | H03-026791 A | 2/1991 |
| JP | H03-052993 A | 3/1991 |
| JP | 2000226589 A * | 8/2000 |
| JP | 2007-154151 A | 6/2007 |
| JP | 2009-235248 A | 10/2009 |
| WO | 2010044562 A2 | 4/2010 |
| WO | 2010109897 A1 | 9/2010 |
| WO | 2012036182 A1 | 3/2012 |

OTHER PUBLICATIONS

Int'l Search Report issued May 29, 2012 in Int'l Application No. PCT/JP2012/057501.
Extended European Search Report issued Aug. 4, 2014 in EP Application No. 12763464.0.

* cited by examiner

*Primary Examiner* — In Suk Bullock
*Assistant Examiner* — Jason Chong
(74) *Attorney, Agent, or Firm* — Panitch Schwarze Belisario & Nadel LLP

(57) ABSTRACT

A method of producing monocyclic aromatic hydrocarbons includes bringing a feedstock oil having a 10 vol % distillation temperature of 140° C. or higher and a 90 vol % distillation temperature of 380° C. or lower, into contact with a catalyst for monocyclic aromatic hydrocarbon production containing a crystalline aluminosilicate, in which a content ratio of monocyclic naphthenobenzenes in the feedstock oil is adjusted to 10 mass % to 90 mass %, by mixing a hydrocarbon oil A having a 10 vol % distillation temperature of 140° C. or higher and a 90 vol % distillation temperature of 380° C. or lower with a hydrocarbon oil B containing more monocyclic naphthenobenzenes than the hydrocarbon oil A.

8 Claims, No Drawings

US 9,573,864 B2

METHOD OF PRODUCING MONOCYCLIC AROMATIC HYDROCARBONS

CROSS-REFERENCE TO RELATED APPLICATION

This application is a Section 371 of International Application No. PCT/JP2012/057501, filed Mar. 23, 2012, which was published in the Japanese language on Oct. 4, 2012, under International Publication No. WO 2012/133180 A1, and the disclosure of which is incorporated herein by reference.

TECHNICAL FIELD

The present invention relates to a method of producing monocyclic aromatic hydrocarbons.

Priority is claimed on Japanese Patent Application No. 2011-067877, filed Mar. 25, 2011, the content of which is incorporated herein by reference.

BACKGROUND ART

In recent years, techniques have been sought that can efficiently produce monocyclic aromatic hydrocarbons having 6 to 8 carbon atoms (such as benzene, toluene, ethylbenzene and xylene, hereinafter, which are collectively referred to as a "BTX fraction" or "BTX"), which can be used as high-octane gasoline base stocks or petrochemical feedstocks and offer high added value, from feedstocks containing a polycyclic aromatic fraction such as a light cycle oil (hereinafter, also referred to as "LCO"), which is a cracked light oil produced by a fluid catalytic cracking (hereinafter, also referred to as "FCC") apparatus, and has been mainly used as light oil or heavy oil fraction.

Examples of known methods for producing a BTX fraction from a polycyclic aromatic fraction include the following methods.

(1) Methods of hydrocracking hydrocarbons containing a polycyclic aromatic fraction in a single stage (see Patent Literatures 1 and 2).

(2) Methods of subjecting hydrocarbons containing a polycyclic aromatic fraction to a hydrotreatment in a preliminary stage and then hydrocracking in a subsequent stage (see Patent Literatures 3 to 5).

(3) A method of converting hydrocarbons containing a polycyclic aromatic fraction directly into a BTX fraction using a zeolite catalyst (see Patent Literature 6).

(4) Methods of converting a mixture of hydrocarbons containing a polycyclic aromatic fraction and light hydrocarbons having 2 to 8 carbon atoms into a BTX fraction using a zeolite catalyst (see Patent Literatures 7 and 8).

However, the methods of (1) and (2) require the addition of high-pressure molecular hydrogen, and there is a problem of a high level of hydrogen consumption. Further, under the hydrogenation conditions, an unnecessary LPG fraction is by-produced in a large amount during production of the target BTX fraction, and not only is energy required to separate the LPG fraction, but also the feedstock efficiency deteriorates.

The method of (3) is not sufficient in terms of conversion of the polycyclic aromatic fraction.

The methods of (4) is designed to improve the thermal balance by combining a production technique for BTX which uses light hydrocarbons as a feedstock and a production technique for BTX which uses hydrocarbons containing a polycyclic aromatic fraction as a feedstock, but is not designed to improve the yield of BTX from the polycyclic aromatic fraction.

CITATION LIST

Patent Literature

[Patent Literature 1] Japanese Unexamined Patent Application, First Publication No. S61-283687
[Patent Literature 2] Japanese Unexamined Patent Application, First Publication No. S56-157488
[Patent Literature 3] Japanese Unexamined Patent Application, First Publication No. S61-148295
[Patent Literature 4] UK Patent No. 1,287,722
[Patent Literature 5] Japanese Unexamined Patent Application, First Publication No. 2007-154151
[Patent Literature 6] Japanese Unexamined Patent Application, First Publication No. H3-2128 [Patent Literature 7] Japanese Unexamined Patent Application, First Publication No. H3-52993
[Patent Literature 8] Japanese Unexamined Patent Application, First Publication No. H3-26791

SUMMARY OF INVENTION

Technical Problem

An object of the present invention is to provide a method of producing a BTX fraction from a fraction containing a light cycle oil (LCO) produced by an FCC apparatus, which enables a more efficient production of the BTX fraction than conventional methods.

Solution to Problem

[1] A method of producing monocyclic aromatic hydrocarbons including bringing a feedstock oil having a 10 vol % distillation temperature of 140° C. or higher and a 90 vol % distillation temperature of 380° C. or lower, into contact with a catalyst for monocyclic aromatic hydrocarbon production containing a crystalline aluminosilicate, in which a content ratio of monocyclic naphthenobenzenes in the feedstock oil is adjusted to 10 mass % to 90 mass %, by mixing a hydrocarbon oil A having a 10 vol % distillation temperature of 140° C. or higher and a 90 vol % distillation temperature of 380° C. or lower with a hydrocarbon oil B containing more monocyclic naphthenobenzenes than the hydrocarbon oil A.

[2] A method of producing monocyclic aromatic hydrocarbons including bringing a feedstock oil having a 10 vol % distillation temperature of 140° C. or higher and a 90 vol % distillation temperature of 380° C. or lower, into contact with a catalyst for monocyclic aromatic hydrocarbon production containing a crystalline aluminosilicate, in which a content ratio of monocyclic naphthenobenzenes in the feedstock oil is adjusted to 10 mass % to 90 mass %, by hydrogenating a hydrocarbon oil A having a 10 vol % distillation temperature of 140° C. or higher and a 90 vol % distillation temperature of 380° C. or lower, or mixing the hydrocarbon oil A with a hydrogenated hydrocarbon oil A.

[3] The method of producing monocyclic aromatic hydrocarbons according to [1] or [2], wherein the content ratio of monocyclic naphthenobenzenes in the feedstock oil is 12 mass % to 90 mass %.

[4] The method of producing monocyclic aromatic hydrocarbons according to any one of [1] to [3], wherein the hydrocarbon oil A contains a light cycle oil which is produced by a fluid catalytic cracking apparatus.

Advantageous Effects of Invention

According to the method of producing monocyclic aromatic hydrocarbons of the present invention, it is possible to produce monocyclic aromatic hydrocarbons having 6 to 8 carbon atoms from a feedstock oil containing polycyclic aromatic hydrocarbons with high yield.

DESCRIPTION OF EMBODIMENTS

A method of producing monocyclic aromatic hydrocarbons according to the present invention includes bringing a feedstock oil having a 10 vol % distillation temperature of 140° C. or higher and a 90 vol % distillation temperature of 380° C. or lower, into contact with a catalyst for monocyclic aromatic hydrocarbon production containing a crystalline aluminosilicate, in which a content ratio of monocyclic naphthenobenzenes in the feedstock oil is adjusted to 10 mass % to 90 mass %, by mixing a hydrocarbon oil A having a 10 vol % distillation temperature of 140° C. or higher and a 90 vol % distillation temperature of 380° C. or lower with a hydrocarbon oil B containing more monocyclic naphthenobenzenes than the hydrocarbon oil A.

A method of producing monocyclic aromatic hydrocarbons according to the present invention includes bringing a feedstock oil having a 10 vol % distillation temperature of 140° C. or higher and a 90 vol % distillation temperature of 380° C. or lower, into contact with a catalyst for monocyclic aromatic hydrocarbon production containing a crystalline aluminosilicate, in which a content ratio of monocyclic naphthenobenzenes in the feedstock oil is adjusted to 10 mass % to 90 mass %, by hydrogenating a hydrocarbon oil A having a 10 vol % distillation temperature of 140° C. or higher and a 90 vol % distillation temperature of 380° C. or lower, or mixing the hydrocarbon oil A with a hydrogenated hydrocarbon oil A.

In the method of producing monocyclic aromatic hydrocarbons according to the present invention, contacting a feedstock with a catalyst for producing monocyclic aromatic hydrocarbons containing a crystalline aluminosilicate converts polyaromatic hydrocarbons to monocyclic aromatic hydrocarbons by partial hydrogenation and ring-opening, using hydrogen transfer between polyaromatic hydrocarbons and saturated hydrocarbons as a hydrogen donor in the feedstock, or converts saturated hydrocarbons in the feedstock, or in those produced during the conversion, to monocyclic aromatic hydrocarbons by cyclization and dehydrogenation. Also, monocyclic aromatic hydrocarbons having 6 to 8 carbon atoms can also be obtained by cracking monocyclic aromatic hydrocarbons having 9 or more carbon atoms. A product containing monocyclic aromatic hydrocarbons is obtained by the complex process of the reaction. Thereby, a product containing monocyclic aromatic hydrocarbons having 6 to 8 carbon atoms and a heavy fraction having 9 or more carbon atoms can be obtained.

This product includes, hydrogen, methane, ethane, ethylene, LPG (propane, propylene, butane, butene and the like), and the like, in addition to the monocyclic aromatic hydrocarbons and the heavy fraction. Furthermore, the heavy fraction includes large amounts of bicyclic aromatic hydrocarbons such as naphthalene, methylnaphthalene, and dimethylnaphthalene, and also includes tricyclic or higher-cyclic aromatic hydrocarbons such as anthracene depending on feedstock oils. In the specification, these bicyclic aromatic hydrocarbons and tricyclic or higher-cyclic aromatic hydrocarbons are collectively described as polycyclic aromatic hydrocarbons.

(Feedstock Oil)

The feedstock oil used in the present invention is an oil having a 10 vol % distillation temperature of 140° C. or higher and a 90 vol % distillation temperature of 380° C. or lower. When an oil having a 10 vol % distillation temperature of lower than 140° C. is used, monocyclic aromatic hydrocarbons are produced by light oil fraction, and therefore, the oil is not suitable for the gist of the present invention. Furthermore, when an oil having a 90 vol % distillation temperature of higher than 380° C. is used, not only the yield of monocyclic aromatic hydrocarbons decreases, but also the amount of coke deposition on the catalyst for monocyclic aromatic hydrocarbon production increases, and the catalytic activity tends to rapidly decrease.

The lower limit of the 10 vol % distillation temperature of the feedstock oil is 140° C. or higher and preferably 150° C. or higher, and the upper limit is preferably 300° C. or lower. In addition, the upper limit of the 90 vol % distillation temperature of the feedstock oil is 380° C. or lower, and preferably 360° C. or lower, and the lower limit is preferably 160° C. or higher.

Here, the 10 vol % distillation temperature and 90 vol % distillation temperature as used herein mean values measured according to JIS K2254 "Petroleum products-Determination of distillation characteristics".

The content ratio of components other than monocyclic naphthenobenzenes in the feedstock oil used in the present invention (monocyclic aromatic fraction, polycyclic aromatic fraction, paraffin fraction, naphthene fraction, and olefin fraction) is not particularly limited and the components may include polycyclic aromatic hydrocarbons such as bicyclic or higher-cyclic aromatic hydrocarbons, saturated hydrocarbons such as paraffin and naphthene, monocyclic aromatic hydrocarbons such as alkyl benzene and the like within the range of not remarkably inhibiting the targeted reaction, or may include hetero atoms such as sulfur, oxygen and nitrogen. When the feedstock oil contains a large amount of polycyclic aromatic hydrocarbons, the yield of monocyclic aromatic hydrocarbons decreases, and therefore, the content of polycyclic aromatic hydrocarbons (polycyclic aromatic fraction) in the feedstock oil is preferably 1 vol % to 50 vol % with respect to 100 vol % of the feedstock, and more preferably 2 vol % to 40 vol %.

The term polycyclic aromatic fraction as used herein means the total value of the content of bicyclic aromatic hydrocarbons (bicyclic aromatic fraction) and the content of tricyclic or higher-cyclic aromatic hydrocarbons (tricyclic or higher-cyclic aromatic fraction), which is measured according to JPI-5S-49 "Petroleum Products—Determination of Hydrocarbon Types—High Performance Liquid Chromatography", or analyzed by an FID gas chromatographic method or a two-dimensional gas chromatographic method. Hereinbelow, when the contents of polycyclic aromatic hydrocarbons, bicyclic aromatic hydrocarbons, and tricyclic or higher-cyclic aromatic hydrocarbons are expressed in vol %, the content has been measured according to JPI-5S-49, while when the content is expressed in mass %, the content has been measured based on an FID gas chromatographic method or a two-dimensional gas chromatographic method.

In addition, in the feedstock oil according to the present invention, the content ratio of monocyclic naphthenobenzenes is adjusted to 10 mass % to 90 mass % with respect to 100 mass % of the feedstock oil, preferably 12 mass % to 90 mass %, and more preferably 15 mass % to 90 mass %.

The term monocyclic naphthenobenzene as used herein means, for example, a compound in which a monocyclic aromatic ring and a naphthene ring coexist in one molecule as in a tetralin skeleton. Specific examples thereof include tetralins, indanes, octahydroanthracenes, octahydrophenanthrenes and the like.

The content ratio (mass %) of monocyclic naphthenobenzenes is measured based on the two-dimensional gas chromatographic method.

In the present invention, the content ratio of monocyclic naphthenobenzenes in the feedstock oil is adjusted to 10 mass % to 90 mass % with respect to 100 mass % of the feedstock oil. The reason is that when the monocyclic naphthenobenzenes are brought into contact with the catalyst for monocyclic aromatic hydrocarbon production used in the present application, the monocyclic naphthenobenzenes can be more efficiently converted to monocyclic aromatic hydrocarbons having 6 to 8 carbon atoms.

While naphthenobenzenes were likely to produce monocyclic aromatic hydrocarbons by a cracking and ring-opening reaction, there was concern that naphthenobenzenes were to produce polycyclic aromatic hydrocarbons by a dehydrogenation reaction, and further, catalytic activity might be decreased by coking these polycyclic aromatic hydrocarbons to be deposited on a catalyst Thus, an increase in the ratio of naphthenobenzenes has not necessarily meant an increase in the yield of monocyclic aromatic hydrocarbons up to now. In addition, when the simple condition for suppressing only dehydrogenation capacity was applied, the cyclization and dehydrogenation of saturated hydrocarbon, which simultaneously proceeded, were suppressed, and therefore, the yield of monocyclic aromatic hydrocarbons could not be increased.

As a result of intensive research, the present inventors found that monocyclic aromatic hydrocarbons could be efficiently produced by using a feedstock oil containing a large amount of monocyclic naphthenobenzenes among naphthenobenzenes and by selecting proper catalysts and reaction conditions, thereby completing the present invention.

The feedstock oil may contain naphthenobenzenes other than monocyclic naphthenobenzenes, but it is not necessarily preferable that the feedstock oil contain a large amount of bicyclic naphthenobenzenes represented by dihydrophenanthrene and tetrahydroanthracene since cracking of an aromatic ring portion is difficult and the yield of monocyclic aromatic hydrocarbons is not improved. However, since the transition to the monocyclic aromatic hydrocarbons can be made by the hydrogen transfer reaction from the saturated hydrocarbons, other polycyclic aromatic hydrocarbons can be contained in the same manner.

Examples of a method of adjusting a content ratio of monocyclic naphthenobenzenes in the feedstock oil to 10 mass % to 90 mass % with respect to 100 mass % of the feedstock oil include the following methods.

(i) A method of mixing a hydrocarbon oil A and a hydrocarbon oil B containing a large amount of monocyclic naphthenobenzenes (ii) A method of hydrogenating a hydrocarbon oil A (iii) A method of mixing a hydrocarbon oil A and a hydrogenated hydrocarbon oil A The hydrocarbon oil A is not particularly limited as long as a 10 vol % distillation temperature is 140° C. or higher and a 90 vol % distillation temperature is 380° C. or lower, and examples thereof include a light cycle oil (LCO) produced by a fluid catalytic cracking (FCC) apparatus, coal liquefied oil, straight run kerosene, straight run light oil, coker kerosene, coker light oil and the like. In the hydrocarbon oil A, the content of monocyclic naphthenobenzenes is preferably 0 mass % to 9.9 mass % with respect to 100 mass % of the hydrocarbon oil A, more preferably 1 mass % to 9.9 mass %, and even more preferably 2 mass % to 9.2 mass %.

The hydrocarbon oil B is not particularly limited as long as the content of monocyclic naphthenobenzenes is more than 10 mass % with respect to 100 mass % of the hydrocarbon oil B, and further, at least, the content of the monocyclic naphthenobenzenes is more than that of the hydrocarbon oil A, but is preferably a hydrocarbon oil having a 10 vol % distillation temperature of 140° C. or higher and a 90 vol % distillation temperature of 380° C. or lower. For example, examples thereof include heavy oil hydrocracked purified oil, oil sand hydrocracked purified oil, oil shale hydrocracked purified oil, and the like. In the hydrocarbon oil B, the content of monocyclic naphthenobenzenes is preferably 10 mass % to 90 mass % with respect to 100 mass % of the hydrocarbon oil B, and more preferably 12 mass % to 90 mass %.

Further, the value of (monocyclic naphthenobenzene content in hydrocarbon oil B)/(monocyclic naphthenobenzene content in hydrocarbon oil A) is preferably 1.1 or more and more preferably 1.5 or more.

In the method of (i), a hydrocarbon oil A and a hydrocarbon oil B containing a large amount of monocyclic naphthenobenzenes may be mixed in advance before the hydrocarbon oil A and the hydrocarbon oil B are put in a reactor, or may be directly mixed in a reactor.

In the case of directly mixing the hydrocarbon oil A with the hydrocarbon oil B in the reactor, a total of the amount of monocyclic naphthenobenzenes in the hydrocarbon oil A and the amount of monocyclic naphthenobenzenes in the hydrocarbon oil B containing a large amount of the monocyclic naphthenobenzenes immediately before the hydrocarbon oil A and the hydrocarbon oil B are put in the reactor, that is, the content of monocyclic naphthenobenzenes in the feedstock oil after the mixing is 10 mass % to 90 mass % with respect to 100 mass % of the feedstock oil after the mixing, preferably 12 mass % to 90 mass %, and more preferably 15 mass % to 90 mass %.

Examples of the method of (ii) include a method of hydrogenating a hydrocarbon oil A. The hydrogenation of the hydrocarbon oil A is carried out for increasing a content of monocyclic naphthenobenzenes. That is, by hydrogenating the hydrocarbon oil A, polycyclic aromatic hydrocarbons contained in the hydrocarbon oil A are partially hydrogenated to produce monocyclic naphthenobenzenes. Therefore, the content of polycyclic aromatic hydrocarbons in the hydrocarbon oil A is preferably 10 mass % to 95 mass % with respect to 100 mass % of the hydrocarbon oil A, more preferably 15 mass % to 95 mass %, and even more preferably 20 mass % to 95 mass %. The content ratio of monocyclic naphthenobenzenes in the hydrocarbon oil A after the hydrogenation is preferably 10 mass % to 90 mass % with respect to 100 mass % of the hydrocarbon oil A after the hydrogenation, and more preferably 12 mass % to 90 mass %. Further, the polycyclic aromatic hydrocarbons are partially hydrogenated and become naphthenobenzenes, but with further hydrogenation, the naphthenobenzenes are converted into naphthenes. The content of naphthenes is not particularly limited, but an excessive naphthene production reduces the content proportion of monocyclic naphthenobenzenes and increases the amount of hydrogen consumption required for hydrogenation, which is not preferable. Therefore, the content of naphthenes is preferably 0.1 mass % to 40 mass % with respect to 100 mass % of the hydrocarbon oil A after the hydrogenation, and more preferably 0.1 mass % to 20 mass %.

Examples of the method of hydrogenating a hydrocarbon oil A preferably include a method of hydrogenating a hydrocarbon oil A in the following conditions.

Examples of the reaction format preferably include fixed bed.

As hydrogenation catalysts, known hydrogenation catalysts (for example, a nickel catalyst, a palladium catalyst, a nickel-molybdenum based catalyst, a cobalt-molybdenum based catalyst, a nickel-cobalt-molybdenum based catalyst, and a nickel-tungsten-based catalyst) can be used.

The hydrogenation reaction temperature may vary depending on the hydrogenation catalyst used, but the hydrogenation reaction temperature is usually set to the range of 100° C. to 450° C., more preferably 200° C. to 400° C., and even more preferably 250° C. to 380° C.

The hydrogenation reaction pressure may vary depending on the hydrogenation catalyst or feedstock used, but the hydrogenation reaction pressure is preferably set to the range of 0.7 MPa to 10 MPa, more preferably set to the range of 1 MPa to 8 MPa, and particularly preferably set to the range of 1 MPa to 6 MPa. When the hydrogenation reaction pressure is 10 MPa or less, the efficient conversion into monocyclic naphthenobenzenes can be made by suppressing the production of naphthenes, and a hydrogenation reactor having a low pressure durability can be used, and the cost of equipment can be reduced. On the other hand, the hydrogenation reaction pressure is preferably 0.7 MPa to 13 MPa from the viewpoint of increasing the content of monocyclic naphthenobenzenes.

The amount of hydrogen consumption is preferably 2500 scfb (422 Nm$^3$/m$^3$) or less, more preferably 1500 scfb (253 Nm$^3$/m$^3$) or less, and even more preferably 1000 scfb (169 Nm$^3$/m$^3$) or less from the viewpoint of efficiently increasing the content of monocyclic naphthenobenzenes by suppressing the production of naphthenes. On the other hand, the amount of hydrogen consumption is preferably 300 scfb (50 Nm$^3$/m$^3$) or greater from the viewpoint of increasing the content of monocyclic naphthenobenzenes. That is, the amount of hydrogen consumption is preferably 300 to 2500 scfb (50 to 422 Nm$^3$/m$^3$), and more preferably 300 to 1500 scfb (50 to 253 Nm$^3$/m$^3$).

The liquid hourly space velocity (LHSV) is preferably set to 0.1 h$^{-1}$ or more to 20 h$^{-1}$ or less, and more preferably set to from 0.2 h$^{-1}$ or more to 10 or less. When the LHSV is set to 20 h$^{-1}$ or less, polycyclic aromatic hydrocarbons can be sufficiently hydrogenated at a lower hydrogenation reaction pressure. On the other hand, when the liquid hourly space velocity (LHSV) is set to 0.1 h$^{-1}$ or more, an excessive increase in the size of a hydrogenation reactor can be avoided. That is, the liquid hourly space velocity (LHSV) is preferably 0.1 h$^{-1}$ to 20 h$^{-1}$, and more preferably 0.2 h$^{-1}$ to 10 h$^{-1}$.

As for the method of (iii), similar to the method of (i), a hydrocarbon oil A and a hydrogenated hydrocarbon oil A may be mixed in advance before the hydrocarbon oil A and the hydrogenated hydrocarbon oil A are put in a reactor, or may be directly mixed in a reactor. The hydrogenation of the hydrocarbon oil A can be carried out in the same manner as in the method of (ii).

The content ratio of monocyclic naphthenobenzenes in the feedstock oil is 10 mass % to 90 mass % with respect to 100 mass % of the feedstock oil, preferably 12 mass % to 90 mass %, and more preferably 15 mass % to 90 mass %.

The upper level of the monocyclic naphthenobenzenes is not particularly limited and it is difficult to prepare the feedstock oil having a content ratio of monocyclic naphthenobenzenes of more than 90 mass % by the methods of (i), (ii) and (iii).

Examples of monocyclic naphthenobenzenes include tetralin, alkyl tetralin, indane, alkyl indane, octahydrophenanthrene, alkyl octahydrophenanthrene, octahydroanthracene, and alkyl octahydroanthracene, but tetralin, alkyl tetralin, indane, and alkyl indane are particularly preferable.

Since these components are mixed in an actual feedstock oil, the separate use of the respective components is not practical and a total amount of these components may be 10 mass % to 90 mass % with respect to 100 mass % of the feedstock oil. Examples of a method of analyzing a content of monocyclic naphthenobenzenes include a method based on a two-dimensional gas chromatographic method.

(Reaction Format)

Examples of the reaction format used when the feedstock oil is brought into contact with a catalyst for monocyclic aromatic hydrocarbon production to react therewith, include a fixed bed, a mobile bed, and a fluidized bed. In the present invention, since heavy fraction are used as a feedstock, a fluidized bed which is capable of continuously removing the coke fraction adhering to the catalyst and is capable of stably carrying out the reaction is preferred. Further, a continuously regenerative type fluidized bed in which a catalyst is circulated between a reactor and a regenerator so that reaction-regeneration can be continuously repeated, is particularly preferred. When brought into contact with the catalyst, the feedstock is preferably in a gas phase. Furthermore, the feedstock may also be diluted with a gas as necessary.

(Catalyst for Monocyclic Aromatic Hydrocarbon Production)

The catalyst according to the present invention contains a crystalline aluminosilicate.

[Crystalline Aluminosilicate]

From the viewpoint of further increasing the yield of monocyclic aromatic hydrocarbons, the crystalline aluminosilicate is preferably a zeolite with medium-sized pores and/or a zeolite with large-sized pores.

The zeolite with medium-sized pores is a zeolite having a 10-membered ring skeletal structure, and examples of the zeolite with medium-sized pores include zeolites having AEL type, EUO type, FER type, HEU type, MEL type, MFI type, NES type, TON type, and WEI type crystal structures. Among these, MFI type zeolite is preferable from the viewpoint that the yield of monocyclic aromatic hydrocarbons can be further increased.

The zeolite with large-sized pores is a zeolite having a 12-membered ring skeletal structure, and examples of the zeolite with large-sized pores include zeolites having AFI type, ATO type, BEA type, CON type, FAU type, GME type, LTL type, MOR type, MTW type, and OFF type crystal structures. Among these, from the viewpoint of industrial applicability, BEA type, FAU type and MOR type zeolites are preferable, and from the viewpoint that the yield of monocyclic aromatic hydrocarbons can be increased, BEA type zeolite is preferable.

The crystalline aluminosilicate may also contain a zeolite with small-sized pores, having a 10-membered or less-membered ring skeletal structure, and a zeolite with ultra-large-sized pores, having a 14-membered or more-membered ring skeletal structure, in addition to the zeolite with medium-sized pores and the zeolite with large-sized pores.

Here, examples of the zeolite with small-sized pores include zeolites having ANA type, CHA type, ERI type, GIS type, KFI type, LTA type, NAT type, PAU type and YUG type crystal structures.

Examples of the zeolite with ultra-large-sized pores include zeolites having CLO type and VPI type crystal structures.

In the case where the reaction format when the feedstock oil is brought into contact with the catalyst for monocyclic aromatic hydrocarbon production is a fixed bed reaction, the content of the crystalline aluminosilicate in the catalyst is preferably 60 mass % to 100 mass %, more preferably 70 mass % to 100 mass %, and particularly preferably 90 mass % to 100 mass %, when the total amount of the catalyst is designated as 100 mass %. When the content of the crystalline aluminosilicate is 60 mass % or more, the yield of monocyclic aromatic hydrocarbons can be sufficiently increased.

In the case where the reaction format when the feedstock oil is brought into contact with the catalyst for monocyclic aromatic hydrocarbon production is a fluidized bed reaction, the content of the crystalline aluminosilicate in the catalyst is preferably 20 mass % to 60 mass %, more preferably 30 mass % to 60 mass %, and particularly preferably 35 mass % to 60 mass %, when the total amount of the catalyst is designated as 100 mass %. When the content of the crystalline aluminosilicate is 20 mass % or more, the yield of monocyclic aromatic hydrocarbons can be sufficiently increased. When the content of the crystalline aluminosilicate is more than 60 mass %, the content of a binder that can be incorporated into the catalyst is decreased, and the catalyst may not be suitable for fluidized bed applications.

[Phosphorus and Boron]

The catalyst for monocyclic aromatic hydrocarbon production preferably contains phosphorus and/or boron. When the catalyst for monocyclic aromatic hydrocarbon production contains phosphorus and/or boron, a decrease in the yield of monocyclic aromatic hydrocarbons over time can be prevented, and coke production on the catalyst surface can be suppressed.

Examples of the method for incorporating phosphorus to the catalyst for monocyclic aromatic hydrocarbon production include a method of supporting phosphorus on a crystalline aluminosilicate, a crystalline aluminogallosilicate or a crystalline aluminozincosilicate, by an ion exchange method, an impregnation method or the like; a method of incorporating a phosphorus compound during zeolite synthesis and substituting a portion in the skeleton of a crystalline aluminosilicate with phosphorus; and a method of using a crystallization accelerator containing phosphorus during zeolite synthesis. The phosphate ion-containing aqueous solution used for incorporating phosphorous to the catalyst is not particularly limited, but solutions prepared by dissolving phosphoric acid, diammonium hydrogen phosphate, ammonium dihydrogen phosphate, and other water-soluble phosphates in water at arbitrary concentrations can be preferably used.

Examples of the method of incorporating boron into the catalyst for monocyclic aromatic hydrocarbon production include a method of supporting boron on a crystalline aluminosilicate, a crystalline aluminogallosilicate or a crystalline aluminozincosilicate, by an ion exchange method, an impregnation method or the like; a method of incorporating a boron compound during zeolite synthesis and substituting a portion of the skeleton of a crystalline aluminosilicate with boron; and a method of using a crystallization accelerator containing boron during zeolite synthesis.

The content of phosphorus and/or boron in the catalyst for monocyclic aromatic hydrocarbon production is preferably 0.1 mass % to 10 mass %, with respect to the total weight of the catalyst, and the lower limit is more preferably 0.5 mass % or more, while the upper limit is more preferably 9 mass % or less, and particularly preferably 8 mass % or less. When the content of phosphorus with respect to the total weight of the catalyst is 0.1 mass % or more, a decrease in the yield of monocyclic aromatic hydrocarbons over time can be prevented, and when the content is 10 mass % or less, the yield of monocyclic aromatic hydrocarbons can be increased.

[Gallium and Zinc]

In the catalyst for monocyclic aromatic hydrocarbon production, gallium and/or zinc can be incorporated as necessary. When gallium and/or zinc is incorporated, the production proportion of monocyclic aromatic hydrocarbons can be further increased.

The form of gallium incorporation in the catalyst for monocyclic aromatic hydrocarbon production may be a form in which gallium is incorporated into the lattice skeleton of a crystalline aluminosilicate (crystalline aluminogallosilicate), a form in which gallium is supported on a crystalline aluminosilicate (gallium-supporting crystalline aluminosilicate), or both of the forms.

The form of zinc incorporation in the catalyst for monocyclic aromatic hydrocarbon production may be a form in which zinc is incorporated into the lattice skeleton of a crystalline aluminosilicate (crystalline aluminozincosilicate), a form in which zinc is supported on a crystalline aluminosilicate (zinc-supporting crystalline aluminosilicate), or both of the forms.

The crystalline aluminogallosilicate and crystalline aluminozincosilicate have a structure in which $SiO_4$, $AlO_4$ and $GaO_4/ZnO_4$ structures exist in the skeletal structure. Furthermore, the crystalline aluminogallosilicate and crystalline aluminozincosilicate are obtained by, for example, gel crystallization by hydrothermal synthesis, a method of inserting gallium or zinc into the lattice skeleton of a crystalline aluminosilicate, or a method of inserting aluminum into the lattice skeleton of a crystalline gallosilicate or a crystalline zincosilicate.

The gallium-supporting crystalline aluminosilicate is a compound in which gallium is supported on a crystalline aluminosilicate according to a known method such as an ion exchange method or an impregnation method. The gallium source used in these methods is not particularly limited, but examples thereof include gallium salts such as gallium nitrate and gallium chloride, and gallium oxide.

The zinc-supporting crystalline aluminosilicate is a compound in which zinc is supported on a crystalline aluminosilicate according to a known method such as an ion exchange method or an impregnation method. The zinc source used in these methods is not particularly limited, but examples thereof include zinc salts such as zinc nitrate and zinc chloride, and zinc oxide.

When the catalyst for monocyclic aromatic hydrocarbon production contains gallium and/or zinc, the content of gallium and/or zinc in the catalyst for monocyclic aromatic hydrocarbon production is preferably 0.01 mass % to 3.0 mass % with respect to 100 mass % of the total amount of the catalyst, and more preferably 0.05 mass % to 1.5 mass %. When the content of gallium and/or zinc is 0.01 mass % or more, the production proportion of monocyclic aromatic hydrocarbons can be further increased. When the content is 3.0 mass % or less, dehydrogenation of naphthenobenzenes is suppressed and thus, monocyclic aromatic hydrocarbons can be produced more efficiently from the feedstock oil.

[Shape]

The catalyst for monocyclic aromatic hydrocarbon production is produced into, for example, a powder form, a granular form, a pellet form or the like according to the reaction format. For example, in the case of a fluidized bed, the catalyst is produced in a powder form, and in the case of a fixed bed, the catalyst is produced in a granular form or a pellet form. The average particle size of the catalyst used in a fluidized bed is preferably 30 µm to 180 µm, and more preferably 50 µm to 100 µm. Further, the bulk density of the catalyst used in a fluidized bed is preferably 0.4 g/cc to 1.8 g/cc, and more preferably 0.5 g/cc to 1.0 g/cc.

The average particle size represents the particle size of 50 mass % in a particle size distribution obtained by classification using sieves, and the bulk density is a value measured by the method of JIS Standards R9301-2-3.

In the case of obtaining a granular or pellet-like catalyst, an oxide which is inert to the catalyst is incorporated as a binder as necessary, and then, the mixture may be molded by using various molding machines.

When the catalyst for monocyclic aromatic hydrocarbon production contains an inorganic oxide such as a binder, a catalyst containing phosphorus as a binder may also be used.

(Reaction Temperature)

Although the reaction temperature when bringing the feedstock oil into contact with the catalyst for monocyclic aromatic hydrocarbon production to react therewith is not particularly limited, the reaction temperature is preferably 400° C. to 650° C. When the lower limit of the reaction temperature is 400° C. or higher, the reaction of the feedstock oil can be facilitated, and the lower limit is more preferably 450° C. or higher. When the upper limit of the reaction temperature is 650° C. or lower, the yield of monocyclic aromatic hydrocarbons can be sufficiently increased, and the upper limit is more preferably 600° C. or lower.

(Reaction Pressure)

The reaction pressure employed when the feedstock oil is brought into contact with the catalyst for monocyclic aromatic hydrocarbon production to react therewith is preferably set to 1.5 MPaG or less, and more preferably to 1.0 MPaG or less. When the reaction pressure is 1.5 MPaG or less, by-production of light gas can be suppressed, and also, pressure resistance of the reaction unit can be lowered. The lower limit of the reaction pressure is not particularly limited, but a normal pressure is preferable from the viewpoint of cost.

(Contact Time)

The contact time between the feedstock oil and the catalyst for monocyclic aromatic hydrocarbon production is not particularly limited so long as the desired reaction substantially proceeds. However, for example, the time for gas passage on the catalyst is preferably 1 second to 300 seconds, and the lower limit is more preferably 5 seconds or longer, while the upper limit is more preferably 150 seconds or shorter.

When the contact time is 1 second or longer, the reaction can be reliably achieved, and when the contact time is 300 seconds or shorter, deposition of carbon matter on the catalyst caused by coking or the like can be suppressed. Also, the amount of light gas generated by cracking can be suppressed.

EXAMPLES

Hereinafter, the invention will be more specifically described based on Examples and Comparative Examples, but the invention is not limited by these Examples.

Preparation Example of Catalyst

Preparation of Catalyst for Monocyclic Aromatic Hydrocarbon Production Containing Crystalline Aluminosilicate A solution (A) composed of 1706.1 g of sodium silicate (J sodium silicate No. 3, $SiO_2$: 28 mass % to 30 mass %, Na: 9 mass % to 10 mass %, balance water, manufactured by Nippon Chemical Industrial Co., Ltd.) and 2227.5 g of water, and a solution (B-1) composed of 64.2 g of $Al_2(SO_4)_3 \cdot 14$ to $18H_2O$ (reagent grade, manufactured by Wako Pure Chemical Industries, Ltd.), 369.2 g of tetrapropylammonium bromide, 152.1 g of $H_2SO_4$ (97 mass %), 326.6 g of NaCl and 2975.7 g of water were each prepared.

Next, while the solution (A) was stirred at room temperature, the solution (B-1) was slowly added to the solution (A). The mixture thus obtained was vigorously stirred for 15 minutes in a mixer, and the gel was crushed to obtain a homogenously fine emulsified-state.

Subsequently, this mixture was placed in an autoclave made of stainless steel, and a crystallization operation was carried out under self-pressure under the conditions including a temperature of 165° C., a time of 72 hours, and a stirring speed of 100 rpm. After completion of the crystallization operation, the product was filtered to collect a solid product, and washing and filtration was repeated 5 times by using about 5 liters of deionized water. The solid obtained by filtration was dried at 120° C., and the solid was calcined at 550° C. for 3 hours under a stream of air.

It was confirmed by an X-ray diffraction analysis that the calcination product thus obtained had an MFI structure. Further, the $SiO_2/Al_2O_3$ ratio (molar ratio) obtained by a MASNMR analysis was 64.8. Furthermore, the content of the aluminum element contained in the lattice structure calculated from these results was 1.32 mass %.

Subsequently, a 30 mass % aqueous solution of ammonium nitrate was added at a ratio of 5 mL per 1 g of the calcination product thus obtained, and the mixture was heated and stirred at 100° C. for 2 hours, subsequently filtered and washed with water. This operation was repeated 4 times, and then the mixture was dried at 120° C. for 3 hours. Thus, an ammonium type crystalline aluminosilicate was obtained. Thereafter, calcination was carried out for 3 hours at 780° C., and thus a proton type crystalline aluminosilicate was obtained.

Subsequently, 120 g of the proton type crystalline aluminosilicate thus obtained was impregnated with 120 g of an aqueous solution of gallium nitrate such that 0.4 mass % (a value calculated with respect to 100 mass % of the total mass of the crystalline aluminosilicate) of gallium would be supported, and the resultant was dried at 120° C. Thereafter, the product was calcined at 780° C. for 3 hours under an air stream, and thus a gallium-supported crystalline aluminosilicate was obtained.

Subsequently, 30 g of the gallium-supported crystalline aluminosilicate thus obtained was impregnated with 30 g of an aqueous solution of diammonium hydrogen phosphate such that 0.7 mass % of phosphorus (a value calculated with respect to 100 mass % of the total mass of the crystalline aluminosilicate) would be supported, and the resultant was dried at 120° C. Thereafter, the product was calcined at 780° C. for 3 hours under an air stream, and thus a catalyst containing a crystalline aluminosilicate, gallium and phosphorus was obtained.

(Catalyst for Fixed Bed)

The crystalline aluminosilicate containing gallium and phosphorus thus obtained was tabletted by applying a pressure of 39.2 MPa (400 kgf), and the catalyst was coarsely crushed and adjusted to a 20 to 28 mesh size. Thus, a granular catalyst (hereinafter, also referred to as "granulated catalyst") was obtained.

(Catalyst for Fluidized Bed)

A mixed solution containing 106 g of sodium silicate (J Sodium Silicate No. 3, $SiO_2$: 28 mass % to 30 mass %, Na: 9 mass % to 10 mass %, remainder: water, manufactured by Nippon Chemical Industrial Co., Ltd.) and pure water was added dropwise to a dilute sulfuric acid to prepare a silica sol aqueous solution ($SiO_2$ concentration: 10.2%). Meanwhile, distilled water was added to 20.4 g of the obtained crystalline aluminosilicate containing gallium and phosphorus to prepare a zeolite slurry. The zeolite slurry was mixed with 300 g of the silica sol aqueous solution, and the resulting slurry was spray dried at 250° C., obtaining a spherically shaped catalyst. Subsequently, the catalyst was calcined for 3 hours at 600° C., obtaining a powdered catalyst (hereinafter, referred to as the "powdered catalyst") having an average particle size of 84 μm and a bulk density of 0.74 g/cc.

Example 1

Example 1 Using Mixture of Hydrocarbon Oil A and Hydrocarbon Oil B (Feedstock Oil)

A light cycle oil (LCO 1) produced by a fluid catalytic cracking apparatus in which the content ratio of monocyclic naphthenobenzenes had not been adjusted was prepared as a hydrocarbon oil A. The composition of the LCO 1 was as follows: a total amount (saturated fraction+olefin fraction) of saturated fraction (total amount of paraffin fraction and naphthene fraction) and unsaturated fraction (olefin fraction): 23 mass, bicyclic naphthene fraction: 1 mass %, monocyclic naphthenobenzene fraction: 9 mass %, monocyclic alkyl benzene fraction: 21 mass %, bicyclic aromatic fraction: 39 mass %, and tricyclic or higher-cyclic aromatic fraction: 9 mass %. The properties of the LCO 1 are shown in Table 1.

A light oil fraction (MHC-GO) containing a large amount of monocyclic naphthenobenzenes and obtained from a mild hydrocracking apparatus was prepared as a hydrocarbon oil B. The composition of the MEC-GO was as follows: a total amount (saturated fraction+olefin fraction) of saturated fraction (total amount of paraffin fraction and naphthene fraction) and unsaturated fraction (olefin fraction): 45 mass, bicyclic naphthene fraction: 14 mass %, monocyclic naphthenobenzene fraction: 25 mass %, monocyclic alkyl benzene fraction: 17 mass %, bicyclic aromatic fraction: 13 mass %, and tricyclic or higher-cyclic aromatic fraction: 0 mass %. The properties of the MHC-GO are shown in Table 1.

Equal masses of the LCO 1 and the MHC-GO were mixed to obtain a feedstock oil 1 having an adjusted content ratio of monocyclic naphthenobenzenes of 17 mass %. The properties of the feedstock oil 1 are shown in Table 2.

The compositions shown in Tables 1 and 2 were analyzed by a method of using a two-dimensional gas chromatography apparatus (manufactured by ZOEX Corp., KT2006 GC×GC system,) and compositions of subsequent hydrocarbon oils and feedstock oils were analyzed in the same manner.

(Monocyclic Aromatic Hydrocarbon Production-Fixed Bed Reaction Test)

Using a fixed bed reactor of which a reactor was filled with 5.5 g of a catalyst for monocyclic aromatic hydrocarbon production, the feedstock oil 1 was brought into contact with a granulated catalyst to react therewith under the conditions including a reaction temperature of 540° C. and a reaction pressure of 0.3 MPaG. The contact time between the feedstock oil 1 and the zeolite component contained in the coarsely crushed catalyst was set to 12 seconds.

When the materials are allowed to react for 30 minutes, and then a composition analysis of a product by gas chromatography directly connected to the apparatus was carried out, the yield of monocyclic aromatic hydrocarbons having 6 to 8 carbon atoms was 37 mass %, and the yield of cracked gas (hydrogen, methane, ethane, ethylene, LPG) was 21 mass %. The results are shown in Table 3.

Example 2

Example 2 Using Mixture of Hydrocarbon Oil A and Hydrocarbon Oil B (Feedstock)

The feedstock oil 1 in Example 1 was used as a feedstock oil.

(Monocyclic Aromatic Hydrocarbon Production-Fluidized Bed Reaction Test)

Using a fluidized bed reaction apparatus of which a reactor was filled with a powered catalyst (400 g), monocyclic aromatic hydrocarbons were produced under the conditions including a reaction temperature of 540° C., a reaction pressure of 0.3 MPaG, a contact time between feedstock oil 1 and the zeolite component contained in the powered catalyst of 12 seconds. As a result, an amount of monocyclic aromatic hydrocarbons having 6 to 8 carbon atoms produced was 34 mass %, and an amount of cracked gas produced was 20 mass %. The results are shown in Table 3.

Example 3

Example 3 Using Mixture of Hydrocarbon Oil A and Hydrocarbon Oil B (Feedstock)

A light cycle oil (LCO 2) produced by a fluid catalytic cracking apparatus in which the content ratio of monocyclic naphthenobenzenes had not been adjusted was prepared as a hydrocarbon oil A. The composition of the LCO 2 was as follows: a total amount (saturated fraction+olefin fraction) of saturated fraction (total amount of paraffin fraction and naphthene fraction) and unsaturated fraction (olefin fraction): 28 mass, bicyclic naphthene fraction: 0 mass %, monocyclic naphthenobenzene fraction: 3 mass %, monocyclic alkyl benzene fraction: 4 mass %, bicyclic aromatic fraction: 52 mass %, and tricyclic or higher-cyclic aromatic fraction: 14 mass %. The properties of the LCO 2 are shown in Table 1.

Equal masses of the LCO2 and the MHC-GO shown in Table 1 were mixed to obtain a feedstock oil 2 having an adjusted content ratio of monocyclic naphthenobenzenes of 14 mass %. The properties of the feedstock oil 2 are shown in Table 2.

(Monocyclic Aromatic Hydrocarbon Production-Fixed Bed Reaction Test)

Reaction was carried out in the same manner as in Example 1 except that the feedstock oil 2 shown in Table 2 was used as a feedstock oil. The yield of monocyclic aromatic hydrocarbons having 6 to 8 carbon atoms was 34 mass %, and the yield of cracked gas was 19 mass %. The results are shown in Table 3.

Example 4

Example 1 Using Hydrogenated Hydrocarbon Oil a as Feedstock Oil (Feedstock)

The LCO 1 shown in Table 1 was hydrogenated using a commercially available nickel-molybdenum catalyst under the conditions including a reaction temperature of 350° C., a reaction pressure of 3 MPa, a LHSV of 0.5 h$^{-1}$, and an amount of hydrogen consumption of 92 Nm$^3$/m$^3$ to obtain a hydrogenated LCO 1. The composition of the hydrogenated LCO 1 was as follows: a total amount (saturated fraction+olefin fraction) of saturated fraction (total amount of paraffin fraction and naphthene fraction) and unsaturated fraction (olefin fraction): 28 mass, bicyclic naphthene fraction: 6 mass %, monocyclic naphthenobenzene fraction: 33 mass %, monocyclic alkyl benzene fraction: 21 mass %, bicyclic aromatic fraction: 12 mass %, and tricyclic or higher-cyclic aromatic fraction: 6 mass %. The properties of the hydrogenated LCO 1 are shown in Table 1.

(Monocyclic Aromatic Hydrocarbon Production-Fixed Bed Reaction Test)

Reaction was carried out in the same manner as in Example 1 except that a feedstock oil 3 (100 mass % of hydrogenated LCO 1) shown in Table 2 was used as a feedstock oil. The yield of monocyclic aromatic hydrocarbons having 6 to 8 carbon atoms was 42 mass %, and the yield of cracked gas was 11 mass %. The results are shown in Table 3.

Example 5

Example 2 Using Hydrogenated Hydrocarbon Oil a as Feedstock Oil (Feedstock)

The LCO 1 shown in Table 1 was hydrogenated using a commercially available nickel-molybdenum catalyst under the conditions including a reaction temperature of 350° C., a reaction pressure of 5 MPa, a LHSV of 0.5 h$^{-1}$, and an amount of hydrogen consumption of 194 Nm$^3$/m$^3$ to obtain a hydrogenated LCO 2. The composition of the hydrogenated LCO 2 was as follows: a total amount (saturated fraction+olefin fraction) of saturated fraction (total amount of paraffin fraction and naphthene fraction) and unsaturated fraction (olefin fraction): 46 mass, bicyclic naphthene fraction: 24 mass %, monocyclic naphthenobenzene fraction: 26 mass %, monocyclic alkyl benzene fraction: 21 mass %, bicyclic aromatic fraction: 5 mass %, and tricyclic or higher-cyclic aromatic fraction: 2 mass %. The properties of the hydrogenated LCO 2 are shown in Table 1.

(Monocyclic Aromatic Hydrocarbon Production-Fixed Bed Reaction Test)

Reaction was carried out in the same manner as in Example 1 except that a feedstock oil 4 (100 mass % of hydrogenated LCO 2) shown in Table 2 was used as a feedstock oil. The yield of monocyclic aromatic hydrocarbons having 6 to 8 carbon atoms was 39 mass %, and the yield of cracked gas was 20 mass %. The results are shown in Table 3.

Example 6

Example 1 Using Mixture of Hydrocarbon Oil and Hydrogenated Hydrocarbon Oil as Feedstock Oil (Feedstock)

Equal masses of the LCO 1 and the hydrogenated LCO 2 shown in Table 1 were mixed to obtain a feedstock oil 5 having an adjusted content ratio of monocyclic naphthenobenzenes of 18 mass %. The properties of the feedstock oil 5 are shown in Table 2.

(Monocyclic Aromatic Hydrocarbon Production-Fixed Bed Reaction Test)

Reaction was carried out in the same manner as in Example 1 except that the feedstock oil 5 shown in Table 2 was used as a feedstock oil. The yield of monocyclic aromatic hydrocarbons having 6 to 8 carbon atoms was 35 mass %, and the yield of cracked gas was 15 mass %. The results are shown in Table 3.

Example 7

Example 2 Using Mixture of Hydrocarbon Oil and Hydrogenated Hydrocarbon Oil as Feedstock Oil (Feedstock)

The LCO 1 and hydrogenated LCO 2 shown in Table 1 were mixed at a mass ratio of 70:30 to obtain a feedstock oil 6 having an adjusted content ratio of monocyclic naphthenobenzenes of 14 mass %. The properties of the feedstock oil 6 are shown in Table 2.

(Monocyclic Aromatic Hydrocarbon Production-Fixed Bed Reaction Test)

Reaction was carried out in the same manner as in Example 1 except that the feedstock oil 6 shown in Table 2 was used as a feedstock oil. The yield of monocyclic aromatic hydrocarbons having 6 to 8 carbon atoms was 34 mass %, and the yield of cracked gas was 13 mass %. The results are shown in Table 3.

Comparative Example 1

Example Using Feedstock Oil with Content Ratio of Monocyclic Naphthenobenzenes Not Adjusted (Feedstock)

The LCO 1 in which the content ratio of monocyclic naphthenobenzenes had not been adjusted was used as a feedstock oil 7. The properties of the feedstock oil 7 are shown in Table 2.

(Monocyclic Aromatic Hydrocarbon Production-Fixed Bed Reaction Test)

Reaction was carried out in the same manner as in Example 1 except that the feedstock oil 7 shown in Table 2 was used as a feedstock oil. The yield of monocyclic aromatic hydrocarbons having 6 to 8 carbon atoms was 32 mass %, and the yield of cracked gas was 10 mass %. The results are shown in Table 3.

From the results shown in Table 3, it was confirmed that monocyclic aromatic hydrocarbons having 6 to 8 carbon atoms could be efficiently produced in Examples 1 to 3 in which the content ratio of monocyclic naphthenobenzenes in the feedstock had been adjusted by using the hydrocarbon oil A and the hydrocarbon oil B in comparison with Comparative Example 1 in which the content ratio of monocyclic naphthenobenzenes had not been adjusted.

Further, it was also confirmed that monocyclic aromatic hydrocarbons having 6 to 8 carbon atoms could be efficiently produced in Examples 4 to 7 in which the content ratio of monocyclic naphthenobenzenes in the feedstock had been adjusted by hydrogenating the hydrocarbon oil in comparison with Comparative Example 1 in which the content ratio of monocyclic naphthenobenzenes had not been adjusted by using the hydrogenated hydrocarbon oil.

TABLE 1

| Properties of hydrocarbon oil | | Analysis method | LCO 1 | LCO 2 | MHC-GO | Hydrogeneated LCO 1 | Hydrogeneated LCO 2 |
|---|---|---|---|---|---|---|---|
| Density at 15° C. (g/cm$^3$) | | JIS K 2249 | 0.933 | 0.954 | 0.876 | 0.915 | 0.896 |
| Dynamic viscosity at 30° C. (mm$^2$/s) | | JIS K 2283 | 3.007 | 6.347 | 2.861 | 2.990 | 2.907 |
| Distillation properties | 10 vol % distillation temperature (° C.) | JIS K 2254 | 213 | 245 | 259 | 211 | 209 |
| | 50 vol % distillation temperature (° C.) | | 262 | 291 | 268 | 260 | 257 |
| | 90 vol % distillation temperature (° C.) | | 343 | 350 | 282 | 341 | 339 |
| Composition analysis | Saturated fraction + unsaturated fraction (mass %) | Gas chromatographic method | 23 | 28 | 45 | 28 | 46 |
| | Bicyclic naphthene fraction (mass %) | | 1 | 0 | 14 | 6 | 24 |
| Monocyclic aromatic | Monocyclic naphthenobenzene fraction (mass %) | | 9 | 3 | 25 | 33 | 26 |
| | Monocyclic alkyl benzene fraction (mass %) | | 21 | 4 | 17 | 21 | 21 |
| Bicyclic aromatic fraction (mass %) | | | 39 | 52 | 13 | 12 | 5 |
| Tricyclic or higher-cyclic aromatic fraction (mass %) | | | 9 | 14 | 0 | 6 | 2 |

TABLE 2

| | | | Example 1 | Example 2 | Example 3 | Example 4 | Example 5 | Example 6 | Example 7 | Comparative Example 1 |
|---|---|---|---|---|---|---|---|---|---|---|
| [Preparation of feedstock oil] | LCO 1 (mass %) | | 50 | 50 | | | | 50 | 70 | 100 |
| | LCO 2 (mass %) | | | | 50 | | | | | |
| | MHC-GO (mass %) | | 50 | 50 | 50 | | | | | |
| | Hydrogenated LCO 1 (mass %) | | | | | 100 | | | | |
| | Hydrogenated LCO 2 (mass %) | | | | | | 100 | 50 | 30 | |

| [Properties of feedstock oil] | | Analysis method | Feedstock oil 1 | Feedstock oil 1 | Feedstock oil 2 | Feedstock oil 3 | Feedstock oil 4 | Feedstock oil 5 | Feedstock oil 6 | Feedstock oil 7 |
|---|---|---|---|---|---|---|---|---|---|---|
| Density at 15° C. (g/cm$^3$) | | JIS K 2249 | 0.904 | 0.904 | 0.915 | 0.915 | 0.896 | 0.915 | 0.922 | 0.933 |
| Dynamic viscosity at 30° C. (mm$^2$/s) | | JIS K 2283 | 2.934 | 2.934 | 4.604 | 2.990 | 2.907 | 2.957 | 2.977 | 3.007 |
| Distillation properties | 10 vol % distillation temperature (° C.) | JIS K 2254 | 225 | 225 | 253 | 211 | 209 | 211 | 211 | 213 |
| | 50 vol % distillation temperature (° C.) | | 263 | 263 | 272 | 260 | 257 | 259 | 260 | 262 |
| | 90 vol % distillation temperature (° C.) | | 319 | 319 | 319 | 341 | 339 | 341 | 341 | 343 |
| Composition analysis | Saturated fraction + unsaturated fraction (mass %) | Gas chromatographic method | 34 | 34 | 37 | 28 | 46 | 35 | 30 | 23 |
| | Bicyclic naphthene fraction (mass %) | | 8 | 8 | 7 | 6 | 24 | 13 | 8 | 1 |
| Monocyclic aromatic | Monocyclic naphthenobenzene fraction (mass %) | | 17 | 17 | 14 | 33 | 26 | 18 | 14 | 9 |
| | Monocyclic alkyl benzene fraction (mass %) | | 19 | 19 | 11 | 21 | 21 | 21 | 21 | 21 |
| Bicyclic aromatic fraction (mass %) | | | 26 | 26 | 33 | 12 | 5 | 22 | 29 | 39 |
| Tricyclic or higher-cyclic aromatic fraction (mass %) | | | 5 | 5 | 7 | 6 | 2 | 6 | 7 | 9 |

TABLE 3

| | | Example 1 | Example 2 | Example 3 | Example 4 | Example 5 | Example 6 | Example 7 | Comparative Example 1 |
|---|---|---|---|---|---|---|---|---|---|
| [Preparation of feedstock oil] | LCO 1 (mass %) | 50 | 50 | | | | 50 | 70 | 100 |
| | LCO 2 (mass %) | | | 50 | | | | | |
| | MHC-GO (mass %) | 50 | 50 | 50 | | | | | |
| | Hydrogenated LCO 1 (mass %) | | | | 100 | | | | |
| | Hydrogenated LCO 2 (mass %) | | | | | 100 | 50 | 30 | |
| | Reaction format | Fixed bed | Fluidized bed | Fixed bed | Fixed bed | Fixed bed | Fixed bed | Fixed bed | Fixed bed |
| | Catalyst | Granulated catalyst | Powdered catalyst | Granulated catalyst | Granulated catalyst | Granulated catalyst | Granulated catalyst | Granulated catalyst | Granulated catalyst |
| Produced amount | Monocyclic aromatic hydrocarbon having 6 to 8 carbon atoms (mass %) | 37 | 34 | 34 | 42 | 39 | 35 | 34 | 32 |
| | Cracked gas (mass %) | 21 | 20 | 19 | 11 | 20 | 15 | 13 | 10 |

INDUSTRIAL APPLICABILITY

The method of producing monocyclic aromatic hydrocarbons according to the present invention is useful for production of monocyclic aromatic hydrocarbons which can be used as high-octane gasoline base stocks or petrochemical feedstocks and offer high added value.

The invention claimed is:

1. A method of producing monocyclic aromatic hydrocarbons comprising:
   (a) preparing a feedstock oil comprising 10 to 90 mass % monocyclic naphthenobenzenes with respect to 100 mass % of the feedstock oil,
   wherein preparing the feedstock oil comprises:
      (i) providing a hydrocarbon oil A having a 10 vol % distillation temperature of 140° C. or higher and a 90 vol % distillation temperature of 380° C. or lower and having greater than 0 and up to 9.9 mass % monocyclic naphthenobenzenes with respect to 100 mass % of the hydrocarbon oil A;
      (ii) providing a hydrocarbon oil B having 10 to 90 mass % monocyclic naphthenobenzenes with respect to 100 mass % of the hydrocarbon oil B; and
      (iii) mixing the hydrocarbon oil A with the hydrocarbon oil B, wherein a value of (monocyclic naphthenobenzenes in the hydrocarbon oil B)/(monocyclic naphthenobenzenes in the hydrocarbon oil A) is 1.1 or more;
   and
   (b) contacting the feedstock oil with a catalyst containing a crystalline aluminosilicate to produce the monocyclic aromatic hydrocarbons.

2. The method of producing monocyclic aromatic hydrocarbons according to claim 1,
   wherein the feedstock oil comprises 12 to 90 mass % monocyclic naphthenobenzenes with respect to 100 mass % of the feedstock oil.

3. The method of producing monocyclic aromatic hydrocarbons according to claim 2,
   wherein the hydrocarbon oil A contains a light cycle oil which is produced by a fluid catalytic cracking apparatus.

4. The method of producing monocyclic aromatic hydrocarbons according to claim 1,
   wherein the hydrocarbon oil A contains a light cycle oil which is produced by a fluid catalytic cracking apparatus.

5. A method of producing monocyclic aromatic hydrocarbons comprising:
   (a) preparing a feedstock oil comprising 10 to 90 mass % monocyclic naphthenobenzenes with respect to 100 mass % of the feedstock oil,
   wherein preparing the feedstock oil comprises:
      (i) providing a hydrocarbon oil A having a 10 vol % distillation temperature of 140° C. or higher and a 90 vol % distillation temperature of 380° C. or lower and having 0 to 9.9 mass % of monocyclic naphthenobenzenes with respect to 100 mass % of the hydrocarbon oil A;
      (ii) dividing the hydrocarbon oil A into a first portion and a second portion;
      (iii) hydrogenating the first portion to produce a hydrogenated hydrocarbon oil A having 10 to 90 mass % monocyclic naphthenobenzenes with respect to 100 mass % of the hydrogenated hydrocarbon oil A; and
      (iv) mixing the second portion with the hydrogenated hydrocarbon oil A;
   and
   (b) contacting the feedstock oil with a catalyst comprising a crystalline aluminosilicate to produce the monocyclic aromatic hydrocarbons.

6. The method of producing monocyclic aromatic hydrocarbons according to claim 5,
   wherein the feedstock oil comprises 12 to 90 mass % monocyclic naphthenobenzenes with respect to 100 mass % of the feedstock oil.

7. The method of producing monocyclic aromatic hydrocarbons according to claim 6,
   wherein the hydrocarbon oil A contains a light cycle oil which is produced by a fluid catalytic cracking apparatus.

8. The method of producing monocyclic aromatic hydrocarbons according to claim 5,
   wherein the hydrocarbon oil A contains a light cycle oil which is produced by a fluid catalytic cracking apparatus.

* * * * *